(12) United States Patent
Choi et al.

(10) Patent No.: US 10,569,260 B2
(45) Date of Patent: Feb. 25, 2020

(54) METHOD FOR PREPARING CATALYST

(71) Applicant: LG CHEM, LTD., Seoul (KR)

(72) Inventors: Byung Yul Choi, Daejeon (KR); Young Hyun Choe, Daejeon (KR); Duk Ki Kim, Daejeon (KR); Hyun Jong Shin, Daejeon (KR); Ju Yeon Park, Daejeon (KR); Hyun Sub Lim, Daejeon (KR); Hyo Sang You, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/075,887

(22) PCT Filed: Oct. 25, 2017

(86) PCT No.: PCT/KR2017/011854
§ 371 (c)(1),
(2) Date: Aug. 6, 2018

(87) PCT Pub. No.: WO2018/093057
PCT Pub. Date: May 24, 2018

(65) Prior Publication Data
US 2019/0060884 A1    Feb. 28, 2019

(30) Foreign Application Priority Data
Nov. 16, 2016  (KR) .................. 10-2016-0152616

(51) Int. Cl.
| | | |
|---|---|---|
| C07C 51/25 | (2006.01) | |
| B01J 27/00 | (2006.01) | |
| B01J 23/00 | (2006.01) | |
| B01J 27/199 | (2006.01) | |
| B01J 27/18 | (2006.01) | |
| B01J 23/88 | (2006.01) | |
| B01J 37/00 | (2006.01) | |
| B01J 23/28 | (2006.01) | |
| C07C 57/04 | (2006.01) | |
| B01J 37/02 | (2006.01) | |
| B01J 37/04 | (2006.01) | |
| B01J 37/08 | (2006.01) | |

(52) U.S. Cl.
CPC .......... *B01J 27/199* (2013.01); *B01J 23/28* (2013.01); *B01J 23/88* (2013.01); *B01J 27/18* (2013.01); *B01J 37/00* (2013.01); *B01J 37/0009* (2013.01); *B01J 37/0036* (2013.01); *B01J 37/0045* (2013.01); *B01J 37/02* (2013.01); *B01J 37/0215* (2013.01); *B01J 37/04* (2013.01); *B01J 37/08* (2013.01); *C07C 51/25* (2013.01); *C07C 51/252* (2013.01); *C07C 57/04* (2013.01); *B01J 2523/00* (2013.01)

(58) Field of Classification Search
CPC ... B01J 23/28; B01J 23/88; B01J 27/18; B01J 27/199; B01J 37/00; B01J 37/0009; B01J 37/0036; B01J 37/0045; B01J 37/02; B01J 37/0215; B01J 37/04; B01J 37/08; C07C 51/25; C07C 51/252; C07C 57/04
See application file for complete search history.

(56) References Cited

U.S. PATENT DOCUMENTS

| | | |
|---|---|---|
| 6,960,684 B2 | 11/2005 | Yunoki et al. |
| 7,220,698 B2 | 5/2007 | Yunoki et al. |
| 7,625,834 B2 | 12/2009 | Naitou et al. |
| 8,178,718 B2 | 5/2012 | Liang et al. |
| 8,252,714 B2 | 8/2012 | Miura et al. |
| 8,361,923 B2 | 1/2013 | Kano et al. |
| 8,426,335 B2 | 4/2013 | Yunoki et al. |
| 8,586,786 B2 | 11/2013 | Miura et al. |
| 9,433,931 B2 | 9/2016 | Choi et al. |
| 9,440,904 B2 | 9/2016 | Nakazawa et al. |
| 2006/0041168 A1 | 2/2006 | Naitou et al. |
| 2007/0032679 A1 | 2/2007 | Naitou et al. |
| 2011/0034326 A1 | 2/2011 | Czaja et al. |
| 2016/0175818 A1* | 6/2016 | Choi ............... B01J 23/8885 562/534 |
| 2016/0207876 A1 | 7/2016 | Mei et al. |

FOREIGN PATENT DOCUMENTS

| | | |
|---|---|---|
| JP | 09313943 A | 12/1997 |
| JP | 2003001113 A | 1/2003 |
| JP | 2004002209 A | 1/2004 |
| JP | 3799660 A | 7/2006 |
| JP | 2008-302313 A | 12/2008 |
| JP | 4295521 B2 | 7/2009 |
| JP | 2009-213970 A | 9/2009 |
| JP | 4691359 B2 | 6/2011 |
| KR | 100746971 B1 | 8/2007 |
| KR | 10-2011-0035966 A | 4/2011 |
| KR | 10-2015-0011391 A | 1/2015 |
| KR | 10-2016-0004252 A | 1/2016 |
| KR | 10-2016-0006594 A | 1/2016 |
| KR | 10-2016-0032037 A | 3/2016 |
| WO | 2015/037611 A1 | 3/2015 |

* cited by examiner

Primary Examiner — Sikarl A Witherspoon
(74) Attorney, Agent, or Firm — Dentons US LLP

(57) ABSTRACT

The present invention relates to a method for preparing a catalyst and a method for preparing unsaturated carboxylic acid using the catalyst prepared according to the preparation method. According to the method for preparing a catalyst, unsaturated carboxylic acid can be provided from an unsaturated aldehyde with a high conversion rate and selectivity.

8 Claims, No Drawings

METHOD FOR PREPARING CATALYST

CROSS-REFERENCE TO RELATED APPLICATION(S)

This application is a National Stage Entry of International Application No. PCT/KR2017/011854, filed on Oct, 25, 2017, and claims the benefit of and priority to Korean Application No. 10-2016-0152616, filed on Nov. 16, 2016, all of which are hereby incorporated by reference in their entirety for all purposes as if fully set forth herein.

TECHNICAL FIELD

The present invention relates to a method for preparing a catalyst and a method for preparing unsaturated carboxylic acid using the catalyst prepared according to the preparation method.

BACKGROUND ART

A process of preparing an unsaturated fatty acid through an unsaturated aldehyde from an olefin is a typical catalytic vapor phase oxidation process. Representative partial oxidation reactions of olefins include: a process of preparing (meth)acrylic acid through (meth)acrolein by the oxidation of propylene or isobutylene; a process of preparing phthalic anhydride by the oxidation of naphthalene or ortho-xylene; and a process of preparing maleic anhydride by the partial oxidation of benzene, butylenes, or butadiene. Among them, (meth)acrylic acid is being applied in various fields such as paints, textile auxiliary agents, coating agents, super absorbent polymers, etc., and thus, demand for high purity (meth)acrylic acid is rapidly increasing.

In general, a metal oxide catalyst used in the oxidation is prepared by a coprecipitation method, a hydrothermal method, sol gel synthesis, physical mixing, etc. In the process of preparing a metal oxide catalyst, a metal precursor is precipitated in the form of a polyanion, a metal oxide, or a metal hydroxide, and the physical properties and morphology of the precipitate vary according to the pH, concentration, reaction time, and aging time of the aqueous solution, and influences the physical state, particle size, and crystal structure of the catalyst.

In Patent Document 1, a technology for preparing a catalyst by coating a powder on a bulk carrier and firing is disclosed. This technology is characterized in that a catalyst drying temperature is 300° C., and a weight reduction rate of a dried material is 5~40 mass %, but such a preparation method causes change in the catalyst structure due to a comparatively high drying temperature, thus deteriorating an unsaturated aldehyde conversion rate and selectivity. Thus, there is an urgent need for studies on a synthesis method that is capable of realizing an excellent unsaturated aldehyde conversion rate and selectivity, and easily providing a catalyst.

PRIOR ART DOCUMENT

Patent Document 1: Japanese Registered Patent No. 4295521

DETAILED DESCRIPTION OF THE INVENTION

Technical Problem

It is an object of the present invention to provide a method for preparing a catalyst.

It is another object of the present invention to provide a method for preparing carboxylic acid using a catalyst prepared according to the above preparation method.

Technical Solution

According to one embodiment of the invention, a method for preparing a catalyst represented by the following Chemical Formula 1, including the steps of: mixing and stirring a metal precursor to prepare a slurry; drying the slurry at 110° C. to 130° C., and grinding, kneading, and conducting first compression molding with it; drying the first compression molded material at 110° C. to 130° C., and grinding and conducting second compression molding with it; and firing the second compression molded material at 300° C. to 500° C., wherein a ligand sublimation rate calculated by the following Mathematical Formula 1 is 0 wt % or more, is provided.

$$\text{Ligand sublimation rate (wt \%)} = \text{amount of sublimed ligand (kg)/amount of ligand before sublimation (kg)} * 100 \quad \text{[Mathematical Formula 1]}$$

$$Mo_{12}P_aA_bB_cC_dD_eE_fO_g \quad \text{[Chemical Formula 1]}$$

In Chemical Formula 1,

A is one or more elements selected from the group consisting of W, V, Nb, and Cr; B is one or more elements selected from the group consisting of As, B, Sb, Ce, Pd, and Te; C is one or more elements selected from the group consisting of Si, Al, Zr, Rh, Cu, Ti, Ag, and Sn; D is one or more elements selected from the group consisting of Na, K, Li, Rb, Cs, Ta, Ca, Mg, Sr, and Ba; and E is one or more elements selected from the group consisting of Fe, Co, and Ni, and a, b, c, d, e, f, and g represent the atomic ratio of each element, where a is 0.5 to 2, b is 0.01 to 10, c is 0 to 15, d is 0.01 to 20, e is 0.01 to 20, f is 0.01 to 15, and g is a value determined by the oxidation state of each atom.

The metal precursor includes a metal and a ligand, and the ligand may be one or more selected from the group consisting of $NH_3$, $NH_2$, $NO_x$ (where x is an integer of 1 to 3), Cl, F, N, OH, $SO_x$ (where x is 3 or 4), O, CO, COO, SCN, CN, NCS, ONO, $C_nH_mO_x$ (where n is an integer of 1 to 20, m is an integer of 1 to 40, and x is an integer of 1 to 10), and a C1-20 alkoxide.

In the step of preparing a slurry, the slurry may be prepared from a metal precursor by a coprecipitation method or a hydrothermal method.

In the step of first compression molding, the slurry may be dried at 110° C. to 130° C. for 8 to 20 hours. In the step of second compression molding, the first compression molded material may be dried at 110° C. to 130° C. for 8 to 20 hours.

The preparation method may further include the step of coating the second compression molded material on an inert carrier, after the step of second compression molding.

According to another embodiment of the invention, a method for preparing unsaturated carboxylic acid, including the steps of supplying an unsaturated aldehyde to a reactor to which a catalyst prepared according to the above preparation method is fixed, and conducting vapor phase oxidation at a temperature of 240° C. to 450° C. and a pressure of 0.1 to 10 atm, is provided.

In the preparation method of unsaturated carboxylic acid, a shell-and-tube heat exchanger type of reactor may be used as the reactor. In the preparation method of unsaturated carboxylic acid, methacrylic acid can be prepared with a high yield using methacrolein as the unsaturated aldehyde, particularly.

Advantageous Effect

According to the method for preparing a catalyst of one embodiment of the present invention, unsaturated carboxylic acid can be provided from an unsaturated aldehyde with a high conversion rate and selectivity.

Best Mode

Hereinafter, a method for preparing a catalyst and a method for preparing unsaturated carboxylic acid using a catalyst prepared by the above preparation method according to specific embodiments of the invention will be explained.

According to one embodiment of the invention, a method for preparing a catalyst represented by the following Chemical Formula 1, including the steps of: mixing and stirring a metal precursor to prepare a slurry; drying the slurry at 110° C. to 130° C., and grinding, kneading, and conducting first compression molding; drying the first compression molded material at 110° C. to 130° C., and grinding and conducting second compression molding with it; and firing the second compression molded material at 300° C. to 500° C., wherein a ligand sublimation rate calculated by the following Mathematical Formula 1 is 0 wt % or more, is provided.

Ligand sublimation rate (wt %)=amount of sublimed ligand (kg)/amount of ligand before sublimation (kg)*100  [Mathematical Formula 1]

$Mo_{12}P_aA_bB_cC_dD_eE_fO_g$  [Chemical Formula 1]

In Chemical Formula 1,

A is one or more elements selected from the group consisting of W, V, Nb, and Cr; B is one or more elements selected from the group consisting of As, B, Sb, Ce, Pd, and Te; C is one or more elements selected from the group consisting of Si, Al, Zr, Rh, Cu, Ti, Ag, and Sn; D is one or more elements selected from the group consisting of Na, K, Li, Rb, Cs, Ta, Ca, Mg, Sr, and Ba; and E is one or more elements selected from the group consisting of Fe, Co, and Ni, and a, b, c, d, e, f, and g represent the atomic ratio of each element, where a is 0.5 to 2, b is 0.01 to 10, c is 0 to 15, d is 0.01 to 20, e is 0.01 to 20, f is 0.01 to 15, and g is a value determined by the oxidation state of each atom.

The metal oxide represented by Chemical Formula 1 has a form of polyoxometalate or heteropoly acid, and can be used in the oxidation of an unsaturated aldehyde to provide unsaturated carboxylic acid with a high conversion rate and selectivity.

In the step of preparing a slurry, a metal precursor including a metal required for the provision of a catalyst of Chemical Formula 1 and a ligand is used. Thus, as the metal precursor, various kinds of metal precursors known in the technical field to which the present invention pertains may be used as long as they include a metal required for the provision of a catalyst of Chemical Formula 1.

For example, the metal precursor may include a metal required for the provision of a catalyst of Chemical Formula 1; and one or more ligands selected from the group consisting of $NH_3$, $NH_2$, $NO_x$ (where x is an integer of 1 to 3), Cl, F, N, OH, $SO_x$ (where x is 3 or 4), O, CO, COO, SCN, CN, NCS, ONO, $C_nH_mO_x$ (where n is an integer of 1 to 20, m is an integer of 1 to 40, and x is an integer of 1 to 10), and a C1-20 alkoxide. More specifically, as the metal precursor, ammonium paramolybdate (($NH_4$)$_6$$Mo_7$$O_{24}$·4$H_2$O), ammonium paratungstate (($NH_4$)$_{10}$$W_{12}$$O_{41}$·5$H_2$O), ammonium metavanadate ($NH_4$$VO_3$), cesium nitrate ($CsNO_3$), copper nitrate (Cu($NO_3$)$_2$·3$H_2$O), iron nitrate (Fe($NO_3$)$_3$·9$H_2$O), antimony trioxide ($Sb_2$$O_3$), molybdenum trioxide ($MoO_3$), vanadium pentoxide ($V_2$$O_5$), etc. may be mentioned. The metal precursor may be used in an appropriate content according to the atomic ratio of each element included in the catalyst of Chemical Formula 1.

In the step of preparing a slurry, in order to provide P of Chemical Formula 1, a metal precursor and phosphoric acid may be mixed together. The content of phosphoric acid may be appropriately controlled according to 'a' of Chemical Formula 1.

In the step of preparing a slurry, the metal precursor may be mixed to prepare a slurry including a catalyst precursor. As a method for mixing the metal precursor, for example, a coprecipitation method or a hydrothermal method may be used.

The slurry prepared through the step of preparing a slurry is dried at 110° C. to 130° C., 115° C. to 125° C. or about 120° C. Here, a drying time may be controlled to about 8 to 20 hours. By drying the slurry under such conditions, more ligands of the metal precursor may be sublimed, and a catalyst capable of improving the unsaturated aldehyde conversion rate and selectivity can be provided.

Thereafter, the obtained dried material may be ground. The grinding may be conducted by various methods known in the technical field to which the present invention pertains. As non-limiting examples, the grinding may be conducted using one selected from the group consisting of a vertical pulverizer, a turbo cutter, a turbo grinder, a rotary cutter mill, a cutter mill, a disc mill, a shred crusher, a crusher, a chopper, and a disc cutter.

Subsequently, the ground material is kneaded. For example, the ground material may be sufficiently kneaded using a kneader so that the viscosity of the ground material may be increased.

In the first compression molding step, the kneaded material is compression molded to prepare a first compression molded material.

The compression molding process may be conducted according to a method known in the technical field to which the present invention pertains. For example, the compression molding may be conducted using extrusion molding equipment. And, for ease of molding, in the compression molding step, molding additives may be further added. More specifically, as the molding additives, polymethacrylate, and/or solvents such as distilled water or alcohols, etc., may be used, and the molding additives may be used in an amount of about 5 to 20 parts by weight, based on 100 parts by weight of the dried and ground material.

In the first compression molding step, the dried and ground material is compression molded in the form of spaghetti, a cylinder, or hollow cylinder to provide a first compression molded material. For example, in the first compression molding step, the dried and ground material may be compression molded in the form of spaghetti to provide a first compression molded material.

The first compression molded material prepared through the first compression molding step is dried at 110° C. to 130° C. again and ground, and then is subjected to second compression molding. In the preparation method according to one embodiment of the present invention, by adopting two compression molding steps, a catalyst capable of improving the unsaturated aldehyde conversion rate and selectivity is provided. The second compression molding step may be progressed as explained in the first compression molding step, and the first compression molding step and the second compression molding step may be progressed under identical conditions or may be differently progressed within the range explained above. For example, in the first and second compression molding steps, the drying temperature may be controlled identically to about 120° C., and the molding additives may not be used in the first compression molding step and the molding additives may be used only in the second compression molding step.

In the second compression molding step, the first compression molded material is dried and ground, and then a second compression molded material in the form of a hollow cylinder, among the spaghetti, cylinder, or hollow cylinder shapes, can be provided.

The preparation method according to one embodiment of the present invention may further include the step of coating the second compression molded material on an inert carrier, after the step of second compression molding. As non-limiting examples of the inert carrier, porous aluminosilicate, silicon carbide, alumina, silica, etc. may be mentioned.

Meanwhile, the preparation method includes the step of firing the second compression molded material at 300° C. to 500° C. Specifically, the second compression molded material may be fired at 300° C. to 450° C., 350° C. to 400° C., or 360° C. to 390° C. to provide a catalyst represented by Chemical Formula 1. Here, the firing time is not specifically limited, and for example, it may be controlled to about 3 to 10 hours.

In the preparation method, the ligand sublimation rate calculated by the following Mathematical Formula 1 may be 0 wt % or more, 0.5 wt % or more, 1.0 wt % or more, or 1.5 wt % or more.

Ligand sublimation rate (wt %)=amount of sublimed ligand (kg)/amount of ligand before sublimation (kg)*100     [Mathematical Formula 1]

The amount of ligand before sublimation means the content of ligand included in a reaction solution in which a metal precursor is dissolved.

According to another embodiment of the invention, a method for preparing unsaturated carboxylic acid, including the steps of supplying an unsaturated aldehyde to a reactor to which a catalyst prepared according to the above preparation method is fixed, and conducting vapor phase oxidation at a temperature of 240° C. to 450° C. and a pressure of 0.1 to 10 atm, is provided.

The method for preparing unsaturated carboxylic acid can provide unsaturated carboxylic acid by oxidation of an unsaturated aldehyde according to the method known in the technical field to which the present invention pertains, except for using a catalyst prepared according to the above explained method for preparing a catalyst. Particularly, the catalyst can provide methacrylic acid with a high conversion rate and selectivity by oxidation of methacrolein.

In the method for preparing unsaturated carboxylic acid, a shell-and-tube heat exchanger type of reactor may be used as the reactor. Specifically, the fixed bed of the shell-and-tube heat exchanger type reactor is filled with the above-explained catalyst, and a mixed gas including an unsaturated aldehyde, oxygen, water vapor, and inert gas may be injected into the reactor. Here, based on the total volume of the mixed gas, the unsaturated aldehyde may be included at 1 to 10 vol %, oxygen may be included at 1 to 20 vol %, water vapor may be included at 10 to 50 vol %, and inert gas may be included at 20 to 80 vol %. Further, the mixed gas may be controlled such that the space velocity of the unsaturated aldehyde may become about 30 to 60 h$^{-1}$.

The oxidation temperature of the unsaturated aldehyde may be controlled to about 240° C. to 450° C., about 240° C. to 340° C., about 240° C. to 310° C., or about 270° C., and the oxidation pressure may be controlled to about 0.1 to 10 atm, about 0.4 to 3 atm, or 1 to 3 atm. The method for preparing unsaturated carboxylic acid can provide unsaturated carboxylic acid with a high yield using the above-explained catalyst.

Hereinafter, the actions and effects of the invention will be explained in more detail through specific examples. However, these are presented only as illustrations of the invention, and the scope of the present invention is not limited thereby.

EXAMPLE 1

Preparation of a Catalyst

In 3000 mL of deionized water, 500 g of ammonium paramolybdate ((NH$_4$)$_6$Mo$_7$O$_{24}$.4H$_2$O), 0.62 g of ammonium paratungstate ((NH$_4$)$_{10}$W$_{12}$O$_{41}$.5H$_2$O), 5.52 g of ammonium metavanadate (NH$_4$VO$_3$), and 46.0 g of cesium nitrate (CsNO$_3$) were dissolved to prepare a first reaction solution.

Meanwhile, in 300 mL of deionized water, 32.65 g of an 85 wt % phosphoric aqueous solution, 11.40 g of copper nitrate (Cu(NO$_3$)$_2$.3H$_2$O), and 28.60 g of iron nitrate (Fe(NO$_3$)$_3$.9H$_2$O) were dissolved to prepare a second reaction solution.

While mixing and stirring the first reaction solution and the second reaction solution, 6.84 g of antimony trioxide (Sb$_2$O$_3$) was added. While continuously stirring the obtained mixed reaction solution, the temperature was raised to 95° C., which was maintained for 3 hours, followed by natural cooling.

The slurry containing the catalyst precursor was dried at about 120° C. for about 15 hours, and then it was ground. The dried and ground material was put into a kneader, and deionized water was added in an amount of about 10 parts by weight, based on 100 parts by weight of the dried and ground material, followed by kneading until the viscosity sufficiently increased. Subsequently, the kneaded material was compression molded in the form of spaghetti.

The compression molded material was dried at about 120° C. for about 15 hours. The catalyst precursor dried in the form of spaghetti was ground. Polymethacrylate (PMMA; average particle diameter: 0.10 μm) powder was added to the dried and ground material as a molding additive in an amount of about 10 parts by weight, based on 100 parts by weight of the dried and ground material, followed by compression molding in the form of a hollow cylinder.

The material molded in the form of a hollow cylinder was fired at about 380° C. for about 5 hours under ventilation of air to prepare a catalyst of the following Chemical Formula 1-1.

P$_{1.2}$Mo$_{12}$W$_{0.01}$V$_{0.2}$Cu$_{0.2}$Fe$_{0.3}$Sb$_{0.1}$Cs$_{1.0}$     [Chemical Formula 1-1]

In Example 1, the ligand sublimation rate calculated by the following Mathematical Formula 1 was 1.6 wt %.

Ligand sublimation rate (wt %)=amount of sublimed ligand (kg)/amount of ligand before sublimation (kg)*100     [Mathematical Formula 1]

COMPARATIVE EXAMPLE 1

Preparation of a Catalyst

In 3000 mL of deionized water, 500 g of ammonium paramolybdate ((NH$_4$)$_6$Mo$_7$O$_{24}$.4H$_2$O), 0.62 g of ammonium paratungstate $((NH_4)_{10}W_{12}O_{41} \cdot 5H_2O)$, 5.52 g of ammonium metavanadate $(NH_4VO_3)$, and 46.0 g of cesium nitrate $(CsNO_3)$ were dissolved to prepare a first reaction solution.

Meanwhile, in 300 mL of deionized water, 32.65 g of an 85 wt % phosphoric aqueous solution, 11.40 g of copper nitrate $(Cu(NO_3)_2 \cdot 3H_2O)$, and 28.60 g of iron nitrate $(Fe(NO_3)_3 \cdot 9H_2O)$ were dissolved to prepare a second reaction solution.

While mixing and stirring the first reaction solution and the second reaction solution, 6.84 g of antimony trioxide $(Sb_2O_3)$ was added. While continuously stirring the obtained mixed reaction solution, the temperature was raised to 95° C., which was maintained for 3 hours, followed by natural cooling.

The slurry containing the catalyst precursor was dried at about 100° C. for about 12 hours, and then it was ground. The dried and ground material was put into a kneader, and deionized water was added in an amount of about 10 parts by weight, based on 100 parts by weight of the dried and ground material, followed by kneading, but the kneading was stopped while sufficient viscosity was not generated, and the kneaded material was compression molded in the form of spaghetti.

The compression molded material was dried at about 100° C. for about 12 hours. The catalyst precursor dried in the form of spaghetti was ground. Polymethacrylate (PMMA; average particle diameter: 0.10 μm) powder was added to the dried and ground material as a molding additive in an amount of about 10 parts by weight, based on 100 parts by weight of the dried and ground material, followed by compression molding in the form of hollow cylinder.

The material molded in the form of a hollow cylinder was fired at about 380° C. for about 5 hours under ventilation of air to prepare a catalyst of the following Chemical Formula 1-1.

$$P_{1.2}Mo_{12}W_{0.01}V_{0.2}Cu_{0.2}Fe_{0.3}Sb_{0.1}Cs_{1.0} \quad \text{[Chemical Formula 1-1]}$$

In Comparative Example 1, the ligand sublimation rate calculated by the above Mathematical Formula 1 was 1.0 wt %.

EXAMPLE 2

Preparation of a Catalyst

To an autoclave, 3000 mL of deionized water, 500 g of molybdenum trioxide $(MoO_3)$, 42.15 g of an 85 wt % phosphoric aqueous solution, and 14.45 g of vanadium pentoxide $(V_2O_5)$ were added, and the solution was stirred at 130° C. for 5 hours to prepare a first reaction solution.

Meanwhile, in 500 mL of deionized water, 25.68 g of iron nitrate $(Fe(NO_3)_3 \cdot 9H_2O)$, 77.44 g of cesium nitrate $(CsNO_3)$, and 15.36 g of copper nitrate $(Cu(NO_3)_2 \cdot 3H_2O)$ were dissolved to prepare a second reaction solution.

The first reaction solution and the second reaction solution were mixed and stirred to obtain a slurry, and then, 190 g of ammonium nitrate $(NH_4NO_3)$ was added, and the solution was continuously stirred.

The obtained slurry containing the catalyst precursor was dried at about 120° C. for about 16 hours, and then it was ground. The dried and ground material was put into a kneader, and deionized water was added in an amount of about 10 parts by weight, based on 100 parts by weight of the dried and ground material, followed by kneading until the viscosity sufficiently increased. Subsequently, the kneaded material was compression molded in the form of spaghetti.

The compression molded material was dried at about 120° C. for about 16 hours. The catalyst precursor dried in the form of spaghetti was ground. Polymethacrylate (PMMA; average particle diameter: 0.10 μm) powder was added to the dried and ground material as a molding additive in an amount of about 10 parts by weight, based on 100 parts by weight of the dried and ground material, followed by compression molding in the form of a hollow cylinder.

The material molded in the form of a hollow cylinder was fired at about 380° C. for about 5 hours under ventilation of air to prepare a catalyst of the following Chemical Formula 1-2.

$$P_{1.5}Mo_{11}V_{0.5}Cu_{0.2}Fe_{0.2}Cs_{1.25} \quad \text{[Chemical Formula 1-2]}$$

(If the atomic ratio of Mo is converted into 12, $P_{1.64}Mo_{12}V_{0.55}Cu_{0.22}Fe_{0.22}Cs_{1.36}$)

In Example 2, the ligand sublimation rate calculated by the above Mathematical Formula 1 was 1.7 wt %.

COMPARATIVE EXAMPLE 2

Preparation of a Catalyst

To an autoclave, 3000 mL of deionized water, 500 g of molybdenum trioxide $(MoO_3)$, 42.15 g of an 85 wt % phosphoric aqueous solution, and 14.45 g of vanadium pentoxide $(V_2O_5)$ were added, and the solution was stirred at 130° C. for 5 hours to prepare a first reaction solution.

Meanwhile, in 500 mL of deionized water, 25.68 g of iron nitrate $(Fe(NO_3)_3 \cdot 9H_2O)$, 77.44 g of cesium nitrate $(CsNO_3)$, and 15.36 g of copper nitrate $(Cu(NO_3)_2 \cdot 3H_2O)$ were dissolved to prepare a second reaction solution.

The first reaction solution and the second reaction solution were mixed and stirred to obtain a slurry, then 190 g of ammonium nitrate $(NH_4NO_3)$ was added, and the solution was continuously stirred.

The obtained slurry containing the catalyst precursor was dried at about 100° C. for about 13 hours, and then it was ground. The dried and ground material was put into a kneader, and deionized water was added in an amount of about 10 parts by weight, based on 100 parts by weight of the dried and ground material, followed by kneading, but the kneading was stopped while sufficient viscosity was not generated, and the kneaded material was compression molded in the form of spaghetti.

The compression molded material was dried at about 100° C. for about 13 hours. The catalyst precursor dried in the form of spaghetti was ground. Polymethacrylate (PMMA; average particle diameter: 0.10 μm) powder was added to the dried and ground material as a molding additive in an amount of about 10 parts by weight, based on 100 parts by weight of the dried and ground material, followed by compression molding in the form of a hollow cylinder.

The material molded in the form of a hollow cylinder was fired at about 380° C. for about 5 hours under ventilation of air to prepare a catalyst of the following Chemical Formula 1-2.

$$P_{1.5}Mo_{11}V_{0.5}Cu_{0.2}Fe_{0.2}Cs_{1.25} \quad \text{[Chemical Formula 1-2]}$$

(If the atomic ratio of Mo is converted into 12, $P_{1.64}Mo_{12}V_{0.55}Cu_{0.2}Fe_{0.22}Cs_{1.36}$)

In Comparative Example 2, the ligand sublimation rate calculated by the above Mathematical Formula 1 was 1.0 wt %.

EXPERIMENTAL EXAMPLE

Evaluation of Catalyst Properties

Using a stainless reactor of which a fixed bed was filled with each catalyst prepared according to the examples and comparative examples, methacrolein was oxidized to prepare methacrylic acid.

Specifically, a mixed gas including 4 vol % of methacrolein, 10 vol % of oxygen, 30 vol % of water vapor, and 55 vol % of nitrogen was introduced into a stainless reactor of which a fixed bed was filled with the catalyst. Here, the introduction speed of the mixed gas was controlled such that the space velocity of methacrolein became 36 h$^{-1}$, and the contact time became 4 seconds. The reaction temperature was controlled to about 240° C. to 310° C., more specifically to about 270° C., and the reaction pressure was controlled to about 1 to 3 atm.

At the beginning of the reaction, the conversion rate, selectivity, and yield were calculated according to the following Mathematical Formulas 2 to 4, and are summarized in Table 1.

Further, after 1000 hours of reaction, the conversion rate, selectivity, and yield were calculated and are summarized in Table 1.

methacrolein conversion rate (mol %)=[mol number of methacrolein reacted/mol number of methacrolein supplied]×100    [Mathematical Formula 2]

methacrolein selectivity (mol %)=[mol number of methacrylic acid produced/mol number of methacrolein reacted]×100    [Mathematical Formula 3]

yield(mol %)=[mol number of methacrylic acid produced/mol number of methacrolein supplied]×100    [Mathematical Formula 4]

The invention claimed is:

1. A method for preparing a catalyst represented by the following Chemical Formula 1, comprising the steps of:
    mixing and stirring a metal precursor to prepare a slurry;
    drying the slurry at 110° C. to 130° C., and grinding, kneading, and conducting first compression molding;
    drying the first compression molded material at 110° C. to 130° C., and grinding and conducting second compression molding; and
    firing the second compression molded material at 300° C. to 500° C.,
    wherein a ligand sublimation rate calculated by the following Mathematical Formula 1 is 0 wt % or more:

ligand sublimation rate (wt %) =amount of sublimed ligand (kg)/amount of ligand before sublimation (kg)*100;    [Mathematical Formula 1]

$$Mo_{12}P_aA_bB_cC_dD_eE_fO_g \quad \text{[Chemical Formula 1]}$$

wherein, in Chemical Formula 1,
    A is one or more elements selected from the group consisting of W, V, Nb, and Cr; B is selected from the group consisting of As, B, Sb, Ce, Pd, and Te; C is selected from the group consisting of Si, Al, Zr, Rh, Cu, Ti, Ag, and Sn; D is selected from the group consisting of Na, K, Li, Rb, Cs, Ta, Ca, Mg, Sr, and Ba; and E is selected from the group consisting of Fe, Co, and Ni, and
    a, b, c, d, e, f, and g represent the atomic ratio of each element, where a is 0.5 to 2, b is 0.01 to 10, c is 0 to 15, d is 0.01 to 20, e is 0.01 to 20, f is 0.01 to 15, and g is a value determined by the oxidation state of each atom.

2. The method for preparing a catalyst according to claim 1, wherein the metal precursor comprises a metal and a ligand, and the ligand is one or more selected from the group consisting of $NH_3$, $NH_2$, $NO_x$ (where x is an integer of 1 to 3), Cl, F, N, OH, $SO_x$ (where x is 3 or 4), O, CO, COO, SCN, CN, NCS, ONO, $C_nH_mO_x$ (where n is an integer of 1 to 20, m is an integer of 1 to 40, and x is an integer of 1 to 10), and a C1-20 alkoxide.

3. The method for preparing a catalyst according to claim 1, wherein the step of preparing a slurry comprises preparing a slurry from the metal precursor by a coprecipitation method or a hydrothermal method.

TABLE 1

|  | Ligand sublimation rate [wt %] | At the beginning of the reaction | | | After 1000 hours of reaction | | |
| --- | --- | --- | --- | --- | --- | --- | --- |
|  |  | Conversion rate | Selectivity | yield | Conversion rate | selectivity | Yield |
| Example 1 | 1.6 wt % | 88.10 | 81.81 | 72.07 | 85.20 | 82.35 | 70.16 |
| Comparative Example 1 | 1.0 wt % | 82.03 | 82.92 | 68.02 | 80.05 | 83.75 | 67.04 |
| Example 2 | 1.7 wt % | 87.16 | 86.20 | 75.13 | 84.40 | 83.33 | 70.33 |
| Comparative Example 2 | 1.0 wt % | 84.80 | 82.14 | 69.65 | 80.70 | 82.50 | 66.58 |

(unit: mol %)

4. The method for preparing a catalyst according to claim 1, wherein the slurry is dried at 110° C. to 130° C. for 8 to 20 hours.

5. The method for preparing a catalyst according to claim 1, wherein the first compression molded material is dried at 110° C. to 130° C. for 8 to 20 hours.

6. The method for preparing a catalyst according to claim 1, further comprising the step of coating the second compression molded material on an inert carrier, after the step of second compression molding.

7. A method for preparing an unsaturated carboxylic acid, comprising the steps of supplying an unsaturated aldehyde to a reactor to which a catalyst prepared according to the method of claim 1 is fixed, and conducting vapor phase oxidation at a temperature of 240° C. to 450° C. and a pressure of 0.1 to 10 atm,
    wherein the unsaturated carboxylic acid is methacrylic acid and the unsaturated aldehyde is methacrolein.

8. The method for preparing unsaturated carboxylic acid according to claim 7, wherein a shell-and-tube heat exchanger type of reactor is used as the reactor.

* * * * *